(12) United States Patent
Ishii et al.

(10) Patent No.: US 8,835,669 B2
(45) Date of Patent: Sep. 16, 2014

(54) METHOD FOR PRODUCING FLUOROSULFURIC ACID ESTER

(75) Inventors: Akihiro Ishii, Kawagoe (JP); Manabu Yasumoto, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/125,452

(22) PCT Filed: Oct. 15, 2009

(86) PCT No.: PCT/JP2009/067841
§ 371 (c)(1),
(2), (4) Date: Apr. 21, 2011

(87) PCT Pub. No.: WO2010/047266
PCT Pub. Date: Apr. 29, 2010

(65) Prior Publication Data
US 2011/0201825 A1    Aug. 18, 2011

(30) Foreign Application Priority Data

Oct. 22, 2008  (JP) ................................. 2008-272020
Dec. 18, 2008  (JP) ................................. 2008-322984

(51) Int. Cl.
C07C 315/02   (2006.01)
C07D 207/16   (2006.01)
C07B 53/00    (2006.01)
C07C 303/24   (2006.01)

(52) U.S. Cl.
CPC .............. *C07D 207/16* (2013.01); *C07B 53/00* (2013.01); *C07C 303/24* (2013.01)
USPC ...................................................... 560/150

(58) Field of Classification Search
CPC .................................................... C07C 315/02
USPC ...................................................... 560/150
See application file for complete search history.

(56) References Cited

U.S. PATENT DOCUMENTS

| 3,733,304 | A | 5/1973 | Firth, Jr. |
| 6,395,918 | B1 | 5/2002 | Loewenthal et al. |
| 2008/0125689 | A1 | 5/2008 | Ishii et al. |
| 2010/0087673 | A1 | 4/2010 | Ishii et al. |

FOREIGN PATENT DOCUMENTS

| ES | 2 136 028 | 11/1999 |
| JP | 2002-512999 A | 5/2002 |
| JP | 2006-290870 A | 10/2006 |
| JP | 2008-201770 A | 9/2008 |
| WO | WO 99/23064 A1 | 5/1999 |

OTHER PUBLICATIONS

Huang et al. (Inorg. Chem., 1986, v. 25, p. 496-98).*
March (March's Advanced Organic Chemistry, 5th ed., (2001)), ch. 10 provided.*
Cady et al. (Inorg. Chem., v. 13, 1974, p. 837-841).*
George A. Olah et al., "Synthetic Methods and Reactions; 88. Sulfuryl Chloride Fluoride, a Convenient Reagent for the Preparation of Amides from Caboxylic Acids and Primary Amines Under Mild Conditions", SYNTHESIS, Aug. 1980, vol. 1980, No. 8, pp. 661-662, XP-002682971.
Gregory P. Roth et al., "Palladium Cross-Coupling Reactions of Aryl Fluorosulfonates: An Alternative to Triflate Chemistry", J. Org. Chem, 1991, vol. 56, No. 11, pp. 3493-3496, XP-002682972.
The Extended European Search Report dated Sep. 21, 2012 (Three (3) pages).
T. S. Chou, et al., Triethylamine Poly(Hydrogen Fluorides) in the Synthesis of Fluorinated Nucleoside Glycon, Tetrahedron Letters (England), 1996, vol. 37, pp. 17-20.
Theodora W. Greene, "Protective Groups in Organic Synthesis", Third Edition, 1999, John Wiley & Sons, Inc. (Twenty-six (26) pages).
A. Focella, et al., "Simple Stereospecific Syntheses of (R)-2-Fluorohexanoic Acid Ethyl Ester", Synthetic Communications (US), 1991, vol. 21, No. 21, pp. 2165-2170.
4th Edition Jikken Kagaku Koza 22 Organic Synthesis IV Acid, Amino acid, Peptide (Maruzen, 1992, p. 214-258) of which page number is changed from 193-309 by the preliminary amendment made on the present application (in Japanese), The Chemical Society of Japan, 1992.
Luc Demange, et al., Practical Synthesis of Boc and Fmoc Protected 4-Fluoro and 4-Difluoroprolines from *Trans*-4-Hydroxyproline, Tetrahedron Letters (UK), 1998, vol. 39, pp. 1169-1172.
International Search Report including English translation dated Dec. 28, 2008 and PCT/ISA/237 Form (Six (6) pages).

* cited by examiner

*Primary Examiner* — Robert Havlin
(74) *Attorney, Agent, or Firm* — Crowell & Moring LLP

(57) ABSTRACT

Fluorosulfuric acid esters can be produced by reacting alcohols with sulfuryl fluoride ($SO_2F_2$) in the presence of a base and water. As a substrate thereof, optically active secondary alcohols are preferable, and optically active α-hydroxyesters and optically active 4-hydroxyprolines are particularly preferable. By performing the reaction in a two-phase system in the presence of a reaction solvent immiscible with water, a desired reaction proceeds particularly well. The present invention is a production method solving all the problems involved in conventional techniques while being industrially practicable.

1 Claim, No Drawings

METHOD FOR PRODUCING FLUOROSULFURIC ACID ESTER

TECHNICAL FIELD

The present invention relates to a method for producing fluorosulfuric acid esters which are important as an intermediate for medicines and agrichemicals.

BACKGROUND OF THE INVENTION

Fluorosulfuric acid esters are important as an intermediate for medicines and agrichemicals. As a production technique relating to the present invention, there are disclosed a method using fluorosulfuric anhydride [$(FSO_2)_2O$] (Patent Publication 1) and a method going through an O—N,N-dialkylsulfamate ester or an imidazole sulfate ester derivative of alcohols (Patent Publication 2 and Non-Patent Publication 1).

The present inventors have disclosed a dehydroxyfluorination reaction of alcohols caused under a combination of sulfuryl fluoride ($SO_2F_2$) and an organic base (Patent Publications 3 and 4).

REFERENCES ABOUT PRIOR ART

Patent Publication

Patent Publication 1: Spanish Patent Publication No. 2136028
Patent Publication 2: Japanese Patent Application Publication No. 2002-512999
Patent Publication 3: Japanese Patent Application Publication No. 2006-290870
Patent Publication 4: Japanese Patent Application Publication No. 2008-201770

Non-Patent Publication

Non-Patent Publication 1: Tetrahedron Letters (England), 1996, volume 37, pages 17-20

SUMMARY OF THE INVENTION

An object of the present invention is to provide a method for practically producing fluorosulfuric acid esters. In order to achieve this, it is necessary to solve the problems involved in conventional techniques.

Concerning Patent Publication 1, it is required to use fluorosulfuric anhydride which is hard to get on a large scale and highly expensive. Additionally, a reaction agent therefor has two fluorosulfonyl ($FSO_2$) groups only one of which is introduced into the target product, which is not preferable also from the viewpoint of atom economy.

Patent Publication 2 and Non-Patent Publication 1 are an indirect production method that goes through a reactive intermediate, in which the intricacies accompanied with the increase of operations, and the increase of wastes become problems.

In Patent Publications 3 and 4, fluorosulfuric acid esters is produced as an active intermediate; however, a reaction for carrying out substitution with a fluorine anion ($F^-$) formed as a by-product in a reaction system proceeds so promptly as not to allow a selective production of the fluorosulfuric acid esters (see Scheme 1). By utilizing the stereochemistry or electronic effect of a substrate, it becomes possible to slow down a subsequent fluorine substitution. However, this case cannot be said to be a production method having a broad substrate-applicable range.

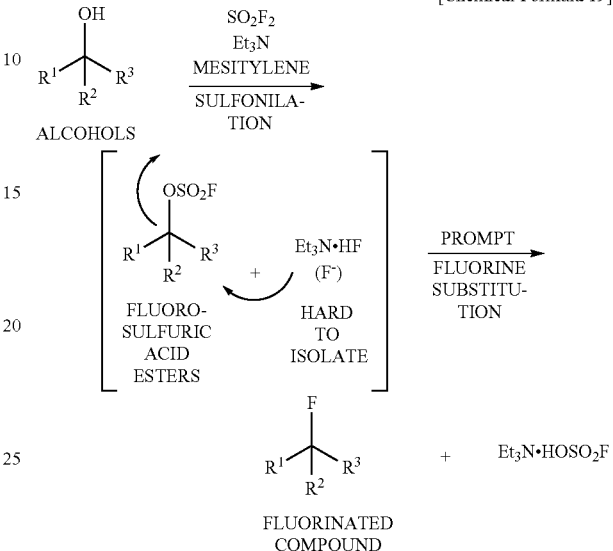

SCHEME 1

[Chemical Formula 19]

CASE OF USING TRIETHYLAMINE AS BASE WHILE USING MESITYLENE AS REACTION SOLVENT

In view of the above, there has been strongly desired a practical production with such a reaction agent so as to be inexpensive, high in atom economy, and readily available on a large scale; a synthesis technique that is a direct manner (convenient operations, few wastes); and such that the substrate-applicable range is broad.

The present inventors had eagerly made studies based on the above-mentioned problems. As a result of this, they found that the fluorosulfuric acid esters can be produced by reacting alcohols with sulfuryl fluoride in the presence of a base and water. Moreover, they disclosed that a desired reaction proceeds particularly well by performing the reaction in a two-phase system in the presence of a reaction solvent immiscible with water. As a substrate, optically active secondary alcohols are preferable, and optically active α-hydroxyesters and optically active 4-hydroxyprolines are particularly preferable. Optically active fluorosulfuric acid esters obtained therefrom are highly important as an intermediate for medicines and agrichemicals.

Production conditions employed in the present invention are similar to those for a dehydroxyfluorination reaction disclosed by Patent Publications 3 and 4. However, it was found that a production ratio of the fluorosulfuric acid esters to fluorinated compounds strikingly reverses according to whether or not the reaction is performed in the presence of water. Table 1 shows comparisons of production ratio obtained in the use of the optically active α-hydroxyesters (a preferable substrate of the present invention), in which the fluorinated compounds are selectively obtained in the absence of water while the fluorosulfuric acid esters are selectively obtained in the presence of water. It is conceivable that a fluorine anion formed in a reaction system as a by-product cannot excellently participate in a subsequent fluorine substitution due to the presence of water (because of reduction of nucleophilicity of the fluorine anion, fixation of the fluorine anion, and the like) and consequently that the fluorosulfuric acid esters (an intermediate) is selectively obtained.

TABLE 1

| Examples | A (R) | $SO_2F_2$ | Base | Reaction Solvent | Reaction Conditions | Conversion Ratio | B:C |
|---|---|---|---|---|---|---|---|
| Patent Publication 3[*1] | 9.6 g ($C_2H_5$) | 1.4 eq | Triethylamine (1.0 eq) | Mesitylene (3.0M) | Room temperature, 22 hours 10 minutes | 100% | 1:99 |
| Patent Publication 4[*2] | 12.0 g ($CH_3$) | 1.2 eq | Triethylamine (1.1 eq) | Not Used | Room temperature, 2 hours 30 minutes | 95% | 1:99[*3] |
| Example 2 | 20.0 g ($C_2H_5$) | 2.0 eq | Triethylamine (1.2 eq) + Potassium carbonate (1.5 eq) | Toluene (1.2M) + Water (1.2M)[*4] | Under ice cooling, 3 hours 30 minutes | 96% | 95:5 |

[*1]Example 4
[*2]Example 1
[*3]Fluorosulfuric acid ester was not detected.
[*4]Two-phase system Thus, an extremely useful method was found as the method for producing the fluorosulfuric acid esters, thereby attaining the present invention.

More specifically, the present invention involves [Invention 1] to [Invention 8] and provides the method for practically producing the fluorosulfuric acid esters.

[Invention 1]

A method for producing a fluorosulfuric acid ester represented by the general formula [2]

[Chemical Formula 3]

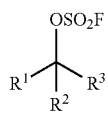

[2]

by reacting an alcohol represented by the general formula [1]

[Chemical Formula 2]

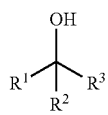

[1]

with sulfuryl fluoride ($SO_2F_2$) in the presence of a base and water.

[In the formulas, $R^1$, $R^2$ and $R^3$ mutually independently represent a hydrogen atom, alkyl group, substituted alkyl group, alkenyl group, substituted alkenyl group, alkynyl group, substituted alkynyl group, aromatic ring group, substituted aromatic ring group, alkylcarbonyl group, substituted alkylcarbonyl group, arylcarbonyl group, substituted arylcarbonyl group, alkoxycarbonyl group, substituted alkoxycarbonyl group, aminocarbonyl group, alkylaminocarbonyl group, substituted alkylaminocarbonyl group, arylaminocarbonyl group, substituted arylaminocarbonyl group, or cyano group. In the case where the total number of groups employing a hydrogen atom and groups employing a cyano group among the three substituents $R^1$, $R^2$ and $R^3$ is 0 or 1, a cyclic structure may be adopted by a covalent bond that carbon atoms of two of the substituents form therebetween, sometimes through a heteroatom.]

[Invention 2]

A method for producing a fluorosulfuric acid ester, as discussed in Invention 1, characterized in that the reaction of Invention 1 is performed in a two-phase system in the presence of a reaction solvent immiscible with water.

[Invention 3]

A method for producing an optically active fluorosulfuric acid ester represented by the general formula [4]

[Chemical Formula 5]

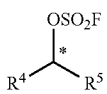

[4]

by reacting an optically active alcohol represented by the general formula [3]

[Chemical Formula 4]

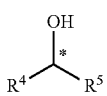

[3]

with sulfuryl fluoride ($SO_2F_2$) in the presence of a base and water.

[In the formulas, $R^4$ and $R^5$ mutually independently represent an alkyl group, substituted alkyl group, alkylcarbonyl group, substituted alkylcarbonyl group, arylcarbonyl group, substituted arylcarbonyl group, alkoxycarbonyl group, substituted alkoxycarbonyl group, aminocarbonyl group, alkylaminocarbonyl group, substituted alkylaminocarbonyl group, arylaminocarbonyl group, substituted arylaminocarbonyl group, or cyano group, and never adopt the same substituent. In the case where $R^4$ or $R^5$ does not adopt a cyano group, a cyclic structure may be adopted by a covalent bond that carbon atoms of two of the substituents form therebetween, sometimes through a heteroatom. "*" represents an asymmetric carbon, and the stereochemistry of the asymmetric carbon is maintained during the reaction.]

[Invention 4]

A method for producing an optically active fluorosulfuric acid ester, as discussed in Invention 3, characterized in that the reaction of Invention 3 is performed in a two-phase system in the presence of a reaction solvent immiscible with water.

[Invention 5]

A method for producing an optically active fluorosulfuric acid ester represented by the general formula [6]

[Chemical Formula 7]

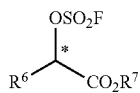

[6]

by reacting an optically active alcohol represented by the general formula [5]

[Chemical Formula 6]

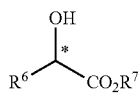

[5]

with sulfuryl fluoride ($SO_2F_2$) in the presence of a base and water.

[In the formulas, $R^6$ and $R^7$ mutually independently represent an alkyl group or substituted alkyl group. $R^6$ and $R^7$ may take on a cyclic structure (e.g., optically active α-hydroxylactones and the like) with a covalent bond that carbon atoms form therebetween, sometimes through a heteroatom. "*" represents an asymmetric carbon, and the stereochemistry of the asymmetric carbon is maintained during the reaction.

[Invention 6]

A method for producing an optically active fluorosulfuric acid ester, as discussed in Invention 5, characterized in that the reaction of Invention 5 is performed in a two-phase system in the presence of a reaction solvent immiscible with water.

[Invention 7]

A method for producing an optically active fluorosulfuric acid ester represented by the general formula [8]

[Chemical Formula 9]

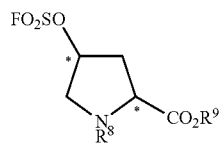

[8]

by reacting an optically active 4-hydroxyproline represented by the general formula [7]

[Chemical Formula 8]

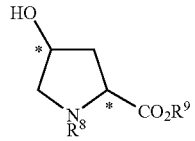

[7]

with sulfuryl fluoride ($SO_2F_2$) in the presence of a base and water.

[In the formulas, $R^8$ represents a protective group for a secondary amino group. $R^9$ represents a protective group for a carboxyl group. Two asterisks "*" mutually independently represent an asymmetric carbon and may mutually independently take on R configuration or S configuration. The stereochemistries of the two asymmetric carbons are maintained during the reaction.

[Invention 8]

A method for producing an optically active fluorosulfuric acid ester, as discussed in Invention 7, characterized in that the reaction of Invention 7 is performed in a two-phase system in the presence of a reaction solvent immiscible with water.

DETAILED DESCRIPTION

Referring now to comparisons with conventional techniques, advantageous points of the present invention will be discussed.

Sulfuryl fluoride used in the present invention is broadly utilized as a fumigant and serves as a reaction agent which is inexpensive, high in atom economy, and readily available on a large scale. Furthermore, a synthesis method thereof is a direct one, so that operations are convenient and wastes are few. In addition to this, control of a subsequent fluorine substitution does not depend on properties of a substrate but depends on production conditions; therefore, a substrate-applicable range thereof is greatly broad.

Furthermore, the present invention hardly provides impurities difficult to separate, so that it is possible to obtain the target product with high chemical purity. Additionally, the stereochemistry of an asymmetric carbon is maintained during the reaction and therefore fluorosulfuric acid esters can be obtained with high optical purity by using alcohols with high optical purity.

Thus the present invention is a production method solving all the problems involved conventional techniques and being industrially practicable.

A method for producing fluorosulfuric acid esters, according to the present invention, will be discussed in detail.

The present invention is a method for producing fluorosulfuric acid esters represented by the general formula [2] by reacting alcohols represented by the general formula [1] with sulfuryl fluoride in the presence of a base and water.

$R^1$, $R^2$ and $R^3$ of the alcohols represented by the general formula [1] mutually independently represent a hydrogen atom, alkyl group, substituted alkyl group, alkenyl group, substituted alkenyl group, alkynyl group, substituted alkynyl group, aromatic ring group, substituted aromatic ring group, alkylcarbonyl group, substituted alkylcarbonyl group, arylcarbonyl group, substituted arylcarbonyl group, alkoxycarbonyl group, substituted alkoxycarbonyl group, aminocarbonyl group, alkylaminocarbonyl group, substituted alkylaminocarbonyl group, arylaminocarbonyl group, substituted arylaminocarbonyl group, or cyano group. Of these, the preferable is an optically active compound in which one of the three substituents employs a hydrogen atom while two other do not employ the same substituent but mutually independently employ alkyl group, substituted alkyl group, alkylcarbonyl group, substituted alkylcarbonyl group, arylcarbonyl group, substituted arylcarbonyl group, alkoxycarbonyl group, substituted alkoxycarbonyl group, aminocarbonyl group, alkylaminocarbonyl group, substituted alkylaminocarbonyl group, arylaminocarbonyl group, substituted arylaminocarbonyl group or cyano group. The particularly preferable are: an optically active compound in which one of the three substituents employs a hydrogen atom and another employs an alkoxycarbonyl group or substituted alkoxycarbonyl group while the last one employs an alkyl group or substituted alkyl group; and an optically active 4-hydroxyproline whose secondary amino group and carboxyl group are protected with protective groups.

Alkyl group may take on a straight or branched chain structure or a ring structure (in the case where the number of carbons is not smaller than 3), having the number of carbons of 1-18. Alkenyl group in the present specification is formed by replacing a single bond formed between any adjacent two carbon atoms of the above-mentioned alkyl group with a double bond, in any number. The stereochemistry of the double bond may be E configuration, Z configuration or a mixture of these [which is also applied to the case where an alkenyl carbon (a $sp^2$ carbon) is not directly bonded to a carbon atom bonded to hydroxyl group]. Alkynyl group in the present specification may replace a single bond between any adjacent two carbon atoms of the above-mentioned alkyl group with a triple bond, in any number [which is also applied to the case where an alkynyl carbon (a sp carbon) is not directly bonded to a carbon atom bonded to hydroxyl group]. Aromatic ring group may be: aromatic hydrocarbon group such as phenyl group, naphthyl group, anthryl group and the like; or aromatic heterocyclic group containing a heteroatom exemplified by a nitrogen atom, oxygen atom, sulfur atom and the like, such as pyrrolyl group, furyl group, thienyl group, indolyl group, benzofuryl group, benzothienyl group and the like. Alkyl group (R) of alkylcarbonyl group (—COR) is the same to the above-mentioned alkyl group. Aryl group (Ar) of arylcarbonyl group (—COAr) is the same to the above-mentioned aromatic ring group. Alkyl group (R) of alkoxycarbonyl group (—CO$_2$R) is the same to the above-mentioned alkyl group. Aminocarbonyl group is represented by —CONH$_2$. Alkyl group (R) of alkylaminocarbonyl group (—CONHR or —CONR$_2$) is the same to the above-mentioned alkyl group. Aryl group (Ar) of arylaminocarbonyl group (—CONHAr or —CONAr$_2$) is the same to the above-mentioned aromatic ring group.

The above-mentioned alkyl group, alkenyl group, alkynyl group, aromatic ring group, alkylcarbonyl group, arylcarbonyl group, alkoxycarbonyl group, alkylaminocarbonyl group and arylaminocarbonyl group may have a substituent at any carbon atom, in any number, and in any combination (they correspond to substituted alkyl group, substituted alkenyl group, substituted alkynyl group, substituted aromatic ring group, substituted alkylcarbonyl group, substituted arylcarbonyl group, substituted alkoxycarbonyl group, substituted alkylaminocarbonyl group and substituted arylaminocarbonyl group, respectively). Examples of the above-mentioned substituent include: a halogen atom such as fluorine, chlorine, bromine and iodine; azide group; nitro group; lower alkyl group such as methyl group, ethyl group, propyl group and the like; lower haloalkyl group such as fluoromethyl group, chloromethyl group, bromomethyl group and the like; lower alkoxy group such as methoxy group, ethoxy group, propoxy group and the like; lower haloalkoxy group such as fluoromethoxy group, chloromethoxy group, bromomethoxy group and the like; lower alkylamino group such as dimethylamino group, diethylamino group, dipropylamino group and the like; lower alkylthio group such as methylthio group, ethylthio group, propylthio group and the like; cyano group; lower alkoxycarbonyl group such as methoxycarbonyl group, ethoxycarbonyl group, propoxycarbonyl group and the like; aminocarbonyl group; lower alkylaminocarbonyl group such as dimethylaminocarbonyl group, diethylaminocarbonyl group, dipropylaminocarbonyl group and the like; unsaturated group such as lower alkenyl group, lower alkynyl group and the like; aromatic ring group such as phenyl group, naphthyl group, pyrrolyl group, furyl group, thienyl group and the like; aromatic ring oxy group such as phenoxy group, naphthoxy group, pyrrolyloxy group, furyloxy group, thienyloxy group and the like; aliphatic heterocyclic group such as piperidyl group, piperidino group, morpholinyl group and the like; hydroxyl group and protected hydroxyl group; amino group (including amino acid and peptide residue) and protected amino group; thiol group and protected thiol group; aldehyde group and protected aldehyde group; carboxyl group and protected carboxyl group; and the like.

In the present specification, the following terms are used respectively with meanings as discussed below. "Lower" means a straight or branched chain structure or a ring structure (in the case where the number of carbons is not smaller than 3) having the number of carbons of 1-6. "Unsaturated group" in the case of having a double bond (alkenyl group) may take both geometrical isomers, i.e., both E configuration and Z configuration. As "protective groups for hydroxyl group, amino group, thiol group, aldehyde group and carboxyl group", protective groups mentioned in "Protective Groups in Organic Synthesis", Third Edition, 1999, John Wiley & Sons, Inc. can be used (it is also possible to protect two or more functional groups simultaneously with one protective group). Moreover, "unsaturated group", "aromatic ring group", "aromatic ring oxy group" and "aliphatic heterocyclic group" may be substituted with a halogen atom, azide group, nitro group, lower alkyl group, lower haloalkyl group, lower alkoxy group, lower haloalkoxy group, lower alkylamino group, lower alkylthio group, cyano group, lower alkoxycarbonyl group, aminocarbonyl group, lower alkylaminocarbonyl group, hydroxyl group, protected hydroxyl group, amino group, protected amino group, thiol group, protected thiol group, aldehyde group, protected aldehyde group, carboxyl group, protected carboxyl group or the like. Though some of these substituents may react with sulfuryl fluoride in the presence of the base and water, it is possible to perform a desired reaction favorably by adopting suitable reaction conditions.

When $R^1$, $R^2$ and $R^3$ of the alcohols represented by the general formula [1] are substituents different from each other, a carbon atom to which a hydroxy group is bonded serves as an asymmetric carbon. The stereochemistry of the asymmetric carbon is maintained during the reaction. In the case where the target compound is an optically active substance, optically active alcohols may be used as the substrate (it will be understood that alcohols in the racemic form may also be used according to the target compound).

In the case where the total number of substituents employing a hydrogen atom and substituents employing a cyano group among the three substituents $R^1$, $R^2$ and $R^3$ of the alcohols represented by the general formula [1] is 0 or 1, a cyclic structure may be adopted by a covalent bond that carbon atoms of two of the substituents form therebetween, sometimes through a heteroatom.

$R^4$ and $R^5$ of optically active alcohols represented by the general formula [3] mutually independently represent an alkyl group, substituted alkyl group, alkylcarbonyl group, substituted alkylcarbonyl group, arylcarbonyl group, substituted arylcarbonyl group, alkoxycarbonyl group, substituted alkoxycarbonyl group, aminocarbonyl group, alkylaminocarbonyl group, substituted alkylaminocarbonyl group, arylaminocarbonyl group, substituted arylaminocarbonyl group, or cyano group, and never adopt the same substituent. These substituents are the same to those corresponding to each of $R^1$, $R^2$ and $R^3$ discussed about the alcohols represented by the general formula [1].

In the case where $R^4$ or $R^5$ of the optically active alcohols represented by the general formula [3] does not adopt a cyano group, a cyclic structure (e.g., optically active hydroxycycloalkanes etc.) may be adopted by a covalent bond that carbon atoms of two of the substituents form therebetween, sometimes through a heteroatom (such as a nitrogen atom, oxygen atom, sulfur atom and the like).

In the general formula [3] showing the optically active alcohols, "*" represents an asymmetric carbon. The stereochemistry of the asymmetric carbon is maintained during the reaction.

As the stereochemistry of the asymmetric carbon of the optically active alcohols represented by the general formula [3], R configuration or S configuration may be suitably used according to the stereochemistry of the target compound. The optical purity thereof is satisfactorily not less than 70% ee, normally preferably not less than 80% ee, and particularly preferably not less than 90% ee.

$R^6$ and $R^7$ of optically active alcohols represented by the general formula [5] mutually independently represent an alkyl group or substituted alkyl group. These substituents are the same to those who correspond to each of $R^1$, $R^2$ and $R^3$ discussed about the alcohols represented by the general formula [1].

The two substituents $R^6$ and $R^7$ of the optically active alcohols represented by the general formula [5] may takes on a cyclic structure (e.g., optically active α-hydroxylactones and the like) with a covalent bond that carbon atoms form therebetween, sometimes through a heteroatom (such as a nitrogen atom, oxygen atom, sulfur atom and the like).

In the general formula [5] showing the optically active alcohols, "*" represents an asymmetric carbon. The stereochemistry of the asymmetric carbon is maintained during the reaction.

As the stereochemistry of the asymmetric carbon of the optically active alcohols represented by the general formula [5], R configuration or S configuration may be suitably used according to the stereochemistry of the target compound. The optical purity thereof is satisfactorily not less than 80% ee, normally preferably not less than 90% ee, and particularly preferably not less than 95% ee.

The optically active alcohols represented by the general formula [5], which serves as a preferable substrate of the present invention, can be produced in the same manner from commercially available various optically active α-amino acids, with reference to Synthetic Communications (the U.S.A.), 1991, volume 21, pages 2165-2170 and the like). Additionally, some alcohols are commercially available, so that a commercially available ethyl ester of (S)-lactic acid was used in Examples. Also concerning either the alcohols represented by the general formula [1] or the optically active alcohols represented by the general formula [3], most of them are commercially available.

$R^8$ of optically active 4-hydroxyprolines shown in the general formula [7] represents a protective group for a secondary amino group. Examples of the protective group include a benzyloxycarbonyl group, tert-butoxycarbonyl group, ρ-fluorenylmethoxycarbonyl group, 3-nitro-2-pyridinesulfenyl group, p-methoxybenzyloxycarbonyl group and the like. Among these, a benzyloxycarbonyl group and tert-butoxycarbonyl group are preferable, and particularly tert-butoxycarbonyl group is preferable. $R^9$ of the optically active 4-hydroxyprolines shown in the general formula [7] represents a protective group for a carboxyl group. Examples of the protective group include a methyl group, ethyl group, tert-butyl group, trichloroethyl group, phenacyl group, benzyl group, 4-nitrobenzyl group, 4-methoxybenzyl group and the like. Among these, a methyl group, ethyl group, tert-butyl group and benzyl group are preferable, and particularly a methyl group and ethyl group are preferable.

The optically active 4-hydroxyprolines represented by the general formula [7], which serves as a preferable substrate of the present invention, can be produced in the same manner from a commercially available optically active 4-hydroxyproline, with reference to 4th Edition Jikken Kagaku Koza 22 Organic Synthesis IV Acid, Amino acid, Peptide (Maruzen, 1992, p. 214-258) and the like. Furthermore, some may be commercially available according to the combination of $R^8$ serving as the protective group for the secondary amino group and $R^9$ serving as the protective group for the carboxyl group, so that it is also possible to use them. Additionally, of the optically active 4-hydroxyprolines represented by the general formula [7], a compound (exhibiting 2-position-S-configuration and 4-position-R-configuration) in which $R^8$ serving as the protective group for the secondary amino group is the tert-butoxycarbonyl group while $R^9$ serving as the protective group for the carboxyl group is the methyl group can be readily produced from hydrochloride of optically active 4-hydroxyproline methyl ester according to Tetrahedron Letters (England), 1998, volume 39, pages 1169-1172.

In the general formula [7] showing the optically active 4-hydroxyprolines, each of two "*" represents an asymmetric carbon. Stereochemistry of each of the two asymmetric carbons is maintained during the reaction.

As stereochemistry of each of the two asymmetric carbons of the optically active 4-hydroxyprolines represented by the general formula [7], there may be suitably adopted 2-position-R-configuration/4-position-R-configuration, 2-position-R-configuration/4-position-S-configuration, 2-position-S-configuration/4-position-R-configuration, or 2-position-S-configuration/4-position-S-configuration, according to stereochemistry of the target compound. The enantiometric excess thereof is satisfactorily not less than 80% ee, preferably not less than 90% ee, and particularly preferably not less than 95% ee. The diastereomeric excess thereof is satisfactorily not less than 80% de, preferably not less than 90% de, and particularly preferably not less than 95% de.

The used amount of sulfuryl fluoride is satisfactorily not lower than 0.7 mol, preferably from 0.8 to 10 mol, and particularly preferably from 0.9 to 5 mol relative to 1 mol of the alcohols represented by the general formula [1].

Examples of the base include: an organic base such as triethylamine, diisopropylethylamine, tri-n-propylamine, tri-n-butylamine, tri-n-pentylamine, pyridine, 2,3-lutidine, 2,4-lutidine, 2,6-lutidine, 3,4-lutidine, 3,5-lutidine, 2,4,6-collidine, 3,5,6-collidine, 4-dimethylaminopyridine, 1,5-diazabicyclo[4,3,0]non-5-ene (DBN), 1,8-diazabicyclo[5,4,0]undec-7-ene (DBU), N,N,N',N',N"-pentamethylguanidine, 1,5,7-triazabicyclo[4,4,0]dec-5-ene (TBD), phosphazene-base such as BEMP and t-Bu-P4, and the like; and an inorganic base such as lithium hydrogencarbonate, sodium hydrogencarbonate, potassium hydrogencarbonate, lithium carbonate, sodium carbonate, potassium carbonate, lithium hydroxide, sodium hydroxide, potassium hydroxide, calcium hydroxide, and the like. Among these, the preferable are triethylamine, diisopropylethylamine, tri-n-butylamine, pyridine, 2,6-lutidine, 2,4,6-collidine, 4-dimethylaminopyridine, 1,5-diazabicyclo[4,3,0]non-5-ene, 1,8-diazabicyclo[5,4,0]undec-7-ene, lithium hydrogencarbonate, potassium hydrogencarbonate, sodium carbonate, potassium carbonate, sodium hydroxide and potassium hydroxide, in which triethylamine, diisopropylethylamine, tri-n-butylamine, 1,8-diazabicyclo[5,4,0]undec-7-ene, lithium hydrogencarbonate, potassium hydrogencarbonate, sodium carbonate and potassium carbonate are particularly preferable. These bases may be used singly or in combination. With the combination of the organic base and the inorganic base, an excellent reactivity and a high selectivity (production ratio; fluorosulfuric acid esters>fluorinated compounds) are sometimes obtained.

When the reaction is conducted in the use of a combination of the organic base and the inorganic base, under preferable production conditions i.e., in a two-phase system in the presence of a reaction solvent immiscible with water, the organic base and the inorganic base are distributed to an organic layer and a water layer, respectively, in a larger amount. In the organic layer, sulfonylation proceeds efficiently with the organic base. In the water layer, a fluorine anion formed as a by-product is efficiently fixed in the form of an alkali metal salt (such as lithium fluoride, sodium fluoride and potassium fluoride) or the like thereby providing an excellent reactivity and a high selectivity. By adopting such preferable production conditions, it becomes possible to produce the target compound with a good reproducibility even on a large scale. In the present specification, "a two-phase system" is a representation directed only to a condition of a liquid phase, so as to be "a three-phase system" in the strict sense if including a gaseous phase in which sulfuryl fluoride is present.

The used amount of the base is satisfactorily not lower than 0.7 mol, preferably from 0.8 to 10 mol, and particularly preferably from 0.9 to 5 mol relative to 1 mol of the alcohols represented by the general formula [1]. In the case of using the bases in combination, the used amount means the total amount of the used bases, in which the one stronger in basicity may be catalytically used (for example, in an amount of 0.1 mol relative to 1 mol of the alcohols).

The used amount of water is satisfactorily not less than 0.05 L (liter), preferably from 0.1 to 30 L, and particularly preferably from 0.2 to 20 L relative to 1 mol of the alcohols represented by the general formula [1]. The used amount of water is an important factor in the production method of the present invention. An excessively small amount of water does not provide a high selectivity, while an excessively large amount of water causes reduction in productivity and increases the economic burden on waste water treatment.

Examples of the reaction solvent immiscible with water include: aliphatic hydrocarbons such as n-hexane, cyclohexane, n-heptane, etc.; aromatic hydrocarbons such as benzene, toluene, xylene, etc.; halogenated hydrocarbons such as methylene chloride, chloroform, 1,2-dichloroethane, etc.; ethers such as diethyl ether, diisopropyl ether, tert-butyl methyl ether, etc.; and esters such as ethyl acetate, n-butyl acetate, etc. Among these, the preferable are n-hexane, n-heptane, toluene, xylene, methylene chloride, diisopropyl ether, tert-butyl methyl ether and ethyl acetate, in which n-heptane, toluene, xylene, tert-butyl methyl ether and ethyl acetate are particularly preferable. These reaction solvents may be used singly or in combination.

The used amount of the reaction solvent immiscible with water is satisfactorily not less than 0.01 L, preferably from 0.03 to 30 L, and particularly preferably from 0.05 to 20 L relative to 1 mol of the alcohols represented by the general formula [1].

The reaction temperature is satisfactorily within the range of from −10 to +150° C., preferably from −5 to +125° C., and particularly preferably from 0 to +100° C.

The reaction time is satisfactorily within 48 hours and changes according to the substrate and the production conditions. It is therefore preferable that a temporal point at which the substrate has been generally completely consumed is regarded as the endpoint of the reaction in such a manner as to trace a reaction-proceeding status by using an analytical device such as gas chromatography, liquid chromatography, nuclear magnetic resonance and the like.

In a post-treatment, a reaction-terminated liquid is separated into two phases to recover organic substances or the organic layer and then diluted with an organic solvent (such as n-hexane, n-heptane, toluene, xylene, methylene chloride, diisopropyl ether, tert-butyl methyl ether, ethyl acetate and the like) as required, followed by performing with water, an aqueous solution of an inorganic acid (such as hydrochloric acid, hydrobromic acid, hydroiodic acid, nitric acid, sulfuric acid and the like) or an aqueous solution of an inorganic base (such as sodium hydrogencarbonate, potassium hydrogencarbonate, sodium carbonate, potassium carbonate, sodium hydroxide, potassium hydroxide and the like), (and further followed by performing drying with a drying agent such as anhydrous sodium sulfate, anhydrous magnesium sulfate and the like, as required). The thus recovered organic substances or organic layer was concentrated, thereby obtaining the fluorosulfuric acid esters represented by the general formula [2], as a crude product. The crude product may be purified at a high chemical purity by an activated carbon treatment, distillation, recrystallization, column chromatography or the like as required. In the case where the fluorosulfuric acid esters (the target compound) are unstable, the recovered organic substances or organic layer may be directly provided to a subsequent reaction.

In the present invention, an alcohol is reacted with sulfuryl fluoride in the presence of a base and water thereby producing a fluorosulfuric acid ester (Embodiment 1).

In Embodiment 1, an optically active secondary alcohol in which one of the three substituents employs a hydrogen atom while two other do not employ the same substituent but mutually independently employ alkyl group, substituted alkyl group, alkylcarbonyl group, substituted alkylcarbonyl group, arylcarbonyl group, substituted arylcarbonyl group, alkoxycarbonyl group, substituted alkoxycarbonyl group, aminocarbonyl group, alkylaminocarbonyl group, substituted alkylaminocarbonyl group, arylaminocarbonyl group, substituted arylaminocarbonyl group or cyano group is preferable as a substrate (Embodiment 2). In this Embodiment the substrate is relatively readily available, and an optically active fluorosulfuric acid ester obtained therein is particularly important as an intermediate for medicines and agrichemicals.

Furthermore, in Embodiment 2, an optically active α-hydroxyester in which one of the three substituents employs a hydrogen atom and another employs an alkoxycarbonyl group or substituted alkoxycarbonyl group while the last one employs an alkyl group or substituted alkyl group is particularly preferable (Embodiment 3). In this Embodiment the substrate is readily available, and an optically active fluorosulfuric acid ester obtained therein is significantly important as the intermediate for medicines and agrichemicals.

In Embodiment 2, furthermore, an optically active 4-hydroxyproline protected with protective groups at a secondary amino group and carboxyl group is particularly preferable as the substrate (Embodiment 4). In this Embodiment the substrate is readily available, and an optically active fluorosulfuric acid ester obtained therein is significantly important as the intermediate for medicines and agrichemicals.

In Embodiments 1, 2, 3 and 4, a desired reaction particularly excellently proceeds by performing the reaction in the two-phase system in the presence of the reaction solvent immiscible with water (Embodiments 5, 6, 7 and 8, respectively).

EXAMPLES

Embodiments of the present invention are specifically explained by examples; however, the present invention is not limited to these examples.

Example 1

A pressure-resistant reaction container formed of stainless steel (SUS) was charged with 1.00 g (8.465 mmol, 1.00 eq) of an alcohol (having a racemic form) represented by the following formula

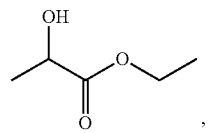

[Chemical Formula 10]

8.5 mL (1.00 M) of toluene, 1.03 g (10.179 mmol, 1.20 eq) of triethylamine and 8.5 mL (1.00 M) of water, followed by immersing the container in an iced bath. Then, 1.73 g (16.951 mmol, 2.00 eq) of sulfuryl fluoride was blown thereinto by using a bomb, followed by stirring it at room temperature all over the night. It was confirmed that the conversion ratio was 81% as a result of $^1$H-NMR analysis of a reaction-terminated liquid (an organic layer). It was confirmed from $^1$H-NMR analysis of the reaction-terminated liquid (the organic layer) that: the production ratio of the alcohol represented by the above formula was 19.4 while a fluorosulfuric acid ester (having a racemic form) represented by the following formula

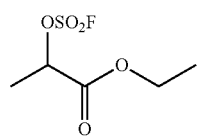

[Chemical Formula 11]

was 80.6; and a fluorinated compound (having a racemic form) represented by the following formula

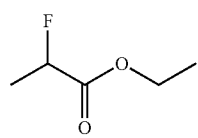

[Chemical Formula 12]

was a trace amount.

The organic layer recovered upon separating the reaction-terminated liquid into two phases was subjected to distillation under reduced pressure within a temperature range of from the boiling point to 90° C. at the reduced pressure of 533 Pa), thereby obtaining 0.37 g of a purified product of the fluorosulfuric acid ester. The yield thereof was 22%. The gas chromatography purity of the purified product was 97.3%.

$^1$H-NMR and $^{19}$F-NMR of the fluorosulfuric acid ester will be discussed below.

$^1$H-NMR [Standard substance; $(CH_3)_4Si$, Deuteration solvent; $CDCl_3$]; δ ppm; 1.33 (t, 7.2Hz, 3H), 1.72 (d, 6.9Hz, 3H), 4.31 (q, 7.2 Hz, 2H), 5.22 (q, 6.9Hz, 1H).

$^{19}$F-NMR [Standard substance; $C_6F_6$, Deuteration solvent; $CDCl_3$]; δ ppm; −63.40 (s, 1F).

Example 2

A pressure-resistant reaction container formed of stainless steel (SUS) was charged with 20.00 g (169.3 mmol, 1.00 eq) of an optically active alcohol (S configuration) represented by the following formula

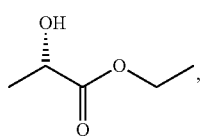

[Chemical Formula 13]

141 mL (1.20 M) of toluene, 20.56 g (203.2 mmol, 1.20 eq) of triethylamine, and 176.10 g of an aqueous solution of potassium carbonate [the aqueous solution was prepared from 35.10 g (254.0 mmol, 1.50 eq) of potassium carbonate and 141 mL (1.20 M) of water], followed by immersing the container in an iced bath. Then, 34.56 g (338.6 mmol, 2.00 eq) of sulfuryl fluoride was blown thereinto by using a bomb, followed by stirring it under ice cooling for three and a half hours. It was confirmed that the conversion ratio was 96% as a result of gas chromatography analysis of a reaction-terminated liquid (an organic layer). At the time of measuring the conversion ratio, it was confirmed that the gas chromatography purity of an optically active fluorosulfuric acid ester (S configuration) represented by the following formula

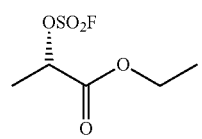

[Chemical Formula 14]

was 82.9% while that of an optically active fluorinated compound (R configuration) represented by the following formula

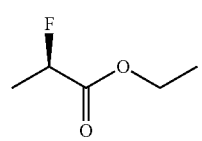

[Chemical Formula 15]

was 4.4%. The production ratio between the optically active fluorosulfuric acid ester and the optically active fluorinated compound was 95:5. The optical purity of the optically active fluorosulfuric acid ester, obtained through chiral gas chromatography analysis of a reaction-terminated liquid (an organic layer), was 97.6% ee (S configuration).

The organic layer recovered upon separating the reaction-terminated liquid into two phases was subjected to distillation under reduced pressure (at the boiling point of 89° C., at the reduced pressure of 3.6 kPa), thereby obtaining 21.13 g of a purified product of the optically active fluorosulfuric acid ester. The yield thereof was 62%. The gas chromatography purity and the optical purity of the purified product was 92.5% and 96.9% ee (S configuration), respectively.

$^1$H-NMR and $^{19}$F-NMR of the optically active fluorosulfuric acid ester were equal to those of the fluorosulfuric acid ester of Example 1 having the racemic form. $^1$H-NMR and $^{19}$F-NMR of the optically active fluorinated compound will be discussed below.

$^1$H-NMR [Standard substance; $(CH_3)_4Si$, Deuteration solvent; $CDCl_3$]; δ ppm; 1.32 (t, 7.2Hz, 3H), 1.58 (dd, 23.6Hz, 6.9Hz, 3H), 4.26 (q, 7.2 Hz, 2H), 5.00 (dq, 49.0Hz, 6.9Hz, 1H).

$^{19}$F-NMR [Standard substance; $C_6F_6$, Deuteration solvent; $CDCl_3$]; δ ppm; −21.88 (dq, 48.9Hz, 24.4Hz, 1F).

Example 3

A pressure-resistant reaction container formed of stainless steel (SUS) was charged with 20.0 g (81.5 mmol, 1.00 eq) of an optically active 4-hydroxyproline (2-position-S-configuration/4-position-R-configuration) represented by the following formula

[Chemical Formula 16]

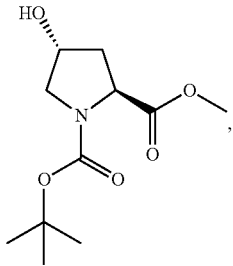

, 68 mL (1.20 M) of toluene, 9.90 g (97.8 mmol, 1.20 eq) of triethylamine, and 84.9 g of an aqueous solution of potassium carbonate [the aqueous solution was prepared from 16.9 g (122 mmol, 1.50 eq) of potassium carbonate and 68 mL (1.20 M) of water], followed by immersing the container in an iced bath. Then, 16.6 g (163 mmol, 2.00 eq) of sulfuryl fluoride was blown thereinto by using a bomb, followed by stirring it under ice cooling all over the night. As a result of liquid chromatography analysis of a reaction-terminated liquid (an organic layer), it was confirmed that the conversion ratio was 86%. In $^{19}$F-NMR analysis of the reaction-terminated liquid (the organic layer), an optically active fluorosulfuric acid ester (2-position-S-configuration/4-position-R-configuration) represented by the following formula

[Chemical Formula 17]

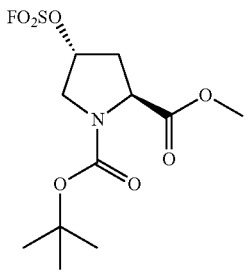

, was detected alone, but an optically active fluorinated compound (2-position-S-configuration/4-position-S-configuration) represented by the following formula

[Chemical Formula 18]

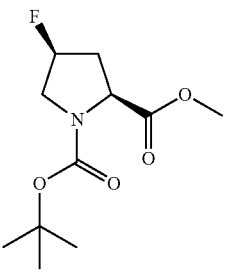

was not detected at all (less than 3 mol %). The reaction-terminated liquid was filtered and separated into two phases, and the organic layer recovered therefrom was subjected to evaporation under reduced pressure and then vacuum drying, thereby obtaining a crude product of the optically active fluorosulfuric acid ester represented by the above formula (the crude product is unstable when stored at room temperature). As a result of quantifying the crude product by $^{19}$F-NMR, 15.5 g of the target compound was confirmed to be included therein. The yield was 58%.

$^1$H-NMR and $^{19}$F-NMR of the optically active fluorosulfuric acid ester will be discussed below (the optically active fluorosulfuric acid ester has an isomer resulting from a tert-butoxycarbonyl group).

$^1$H-NMR [Standard substance; $(CH_3)_4Si$, Deuteration solvent; $CDCl_3$]; δ ppm; 1.43 (s, a part of 9H), 1.48 (s, a part of 9H), 2.34 (m, 1H), 2.74 (m, 1H), 3.77 (s, 3H), 3.79 (m, 1H), 3.99 (m, 1H), 4.47 (m, 1H), 5.45 (m, 1H).

$^{19}$F-NMR [Standard substance; $C_6F_6$, Deuteration solvent; $CDCl_3$]; δ ppm; 201.66 (s, a part of 1F), 201.80 (s, a part of 1F).

To 4.5 mL (0.75 M) of toluene, 1.11 g (equals 3.38 mmol, 1.00 eq) of the crude product of the optically active fluorosulfuric acid ester represented by the above formula and 3.27 g (10.0 mmol, 2.96 eq) of tetrabutylammonium bromide were added, followed by stirring at room temperature all over the night. The conversion ratio obtained by $^1$H-NMR analysis of a reaction mixture liquid was 100%. A reaction-terminated liquid was washed with 2 mL of water six times, and an organic layer recovered therefrom was subjected to evaporation under reduced pressure and then vacuum drying, thereby obtaining 0.447 g of a crude product of an optically active brominated compound (2-position-S-configuration/4-position-S-configuration) represented by the following formula

[Chemical Formula 19]

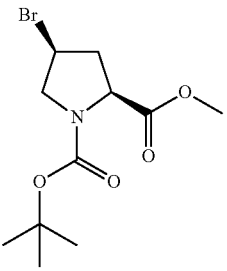

The yield was 43%.

$^1$H-NMR of the optically active brominated compound will be discussed below (the optically active brominated compound has an isomer resulting from a tert-butoxycarbonyl group).

$^1$H-NMR [Standard substance; $(CH_3)_4Si$, Deuteration solvent; $CDCl_3$]; δ ppm; 1.42 (s, a part of 9H), 1.47 (s, a part of 9H), 2.42 (m, 1H), 2.84 (m, 1H), 3.73 (m, 1H), 3.77 (s, 3H), 4.06 (m, 1H), 4.20-4.50 (m, 2H).

The invention claimed is:

1. A method for producing a fluorosulfuric acid ester represented by the formula

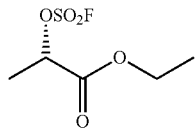

by reacting an alcohol represented by the formula

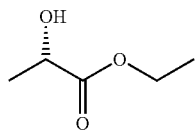

with sulfuryl fluoride ($SO_2F_2$) in the presence of a base and water,
  wherein the reaction is performed in a two-phase system in the presence of a reaction solvent immiscible with water, the base is triethylamine and potassium carbonate, and the reaction solvent immiscible with water is toluene.

* * * * *